United States Patent [19]

Shefter et al.

[11] 4,368,197
[45] Jan. 11, 1983

[54] ZINC AMINOPHYLLINE AND ITS USE IN THE TREATMENT OF BRONCHOSPASMS

[75] Inventors: Eli Shefter, Williamsville; Francis X. Smith, Webster; Mark J. Gardner, Kenmore, all of N.Y.

[73] Assignee: Research Corporation, New York, N.Y.

[21] Appl. No.: 204,861

[22] Filed: Nov. 7, 1980

Related U.S. Application Data

[63] Continuation of Ser. No. 13,266, Feb. 21, 1979, abandoned.

[51] Int. Cl.³ .................. A61K 31/555; C07F 3/06; C07F 9/66
[52] U.S. Cl. .................. 424/245; 424/253; 544/226; 544/267
[58] Field of Search .............. 424/245, 253; 544/226, 544/267

[56] References Cited

U.S. PATENT DOCUMENTS

| | | | |
|---|---|---|---|
| 2,008,252 | 7/1935 | Jostes et al. | 426/245 |
| 2,667,439 | 1/1954 | Marty | 424/253 |
| 3,830,824 | 8/1974 | Margraf | 260/299 |
| 3,830,825 | 8/1974 | Margraf | 260/299 |
| 3,830,908 | 8/1974 | Kuippel et al. | 424/28 |
| 3,856,805 | 12/1974 | Margraf | 260/299 |
| 4,031,218 | 6/1977 | El-Antably | 424/253 |
| 4,049,802 | 9/1977 | Fox | 424/229 |
| 4,085,214 | 4/1978 | Higuchi et al. | 424/253 |

*Primary Examiner*—Leonard Schenkman
*Attorney, Agent, or Firm*—Oblon, Fisher, Spivak, McClelland & Maier

[57] ABSTRACT

There is disclosed zinc complexes of amine salts of theophylline. The preferred compound disclosed is the zinc complex of aminophylline. These compounds are useful as bronchodilators and have antibronchospasmotic activity. They are substantially insoluble and do not impart an unpleasant taste to oral formulations. In addition, they are storage stable. The compounds are prepared by reacting a water soluble simple zinc salt with the amine salt of theophylline at temperatures of from 60°–90° C. for about 8 to 16 hours.

6 Claims, 3 Drawing Figures

ZINC AMINOPHYLLINE AND ITS USE IN THE TREATMENT OF BRONCHOSPASMS

This is a continuation, of application Ser. No. 013,266, filed Feb. 21, 1979, now abandoned.

BACKGROUND OF THE INVENTION

Theophylline is a naturally occurring xanthine alkaloid with potent bronchodilator properties. It is especially useful for treating bronchial asthma and is widely used to treat asthma in children. Theophylline's acceptability by patients, particularly children, is reduced because it has a very bitter taste which is difficult to mask. Children and a portion of the adult population may have difficulty in swallowing tablets and capsules and hence require dosage forms of chewable tablets or liquids. Since these latter dosage forms must have an acceptable taste, it is difficult to formulate theophylline into such oral formulations.

Aminophylline, the ethylenediamine salt of theophylline which is a commonly used form of theophylline, also has an unacceptability bitter taste.

Because theophylline and aminophylline are water soluble, 8 mg/ml and 200 mg/ml at room temperature respectively, it is difficult to mask their bitter tastes, the reason oral administration to children is difficult if not impossible.

In addition to the taste problem, orally administered aminophylline and theophylline can cause undesirable side effects, particularly gastric distress and irritation. One potential cause for this, in the case of aminophylline, is that aminophylline is rapidly hydrolyzed in the acidic environment of the stomach releasing large amounts of free theophylline and ethylenediamine very quickly.

Theophylline has a narrow therapeutic range and blood concentrations above this range can cause toxic side effects. Because of the solubility of theophylline and aminophylline, it is very difficult to control the blood concentration pattern of theophylline to keep it in the acceptable therapeutically effective range.

If administered as aminophylline, all the theophylline is released very rapidly into the stomach where it is absorbed and reaches a peak blood concentration very quickly. This peak can easily be in the toxic range since effective dosages are very close to the toxic level. This can be overcome by more frequent administrations while decreasing the dosage per administration, a generally unacceptable approach.

If administered as theophylline per se, the theophylline is absorbed very quickly and rapidly produces peak concentrations in the bloodstream, also resulting in possible toxic effects.

Reports in the literature with a variety of theophylline derivatives show that the theophylline blood concentrations achieved in many instances are below the values required for relief of bronchospasm and even when therapeutic concentrations are obtained, they fall off extremely rapidly in the first few hours following administration of the drug. Thus repeated dosing of the patient about every three to four hours is necessary. Generally the drug is administered orally, although it can be parenterally administered. Oral administration is preferred because of the frequency of administration required and the patient's convenience.

On exposure to air aminophylline will gradually lose ethylenediamine and absorb carbon dioxide. This creates a stability problem that can be controlled by careful formulation of the dosage form and proper storage conditions.

There is a need for a storage stable theophylline compound having an acceptable taste and chemical characteristics which make available suitable therapeutic blood levels of theophylline and maintain these blood levels for a sufficient length of time to reduce or eliminate the danger of undesirable side effects.

SUMMARY OF THE INVENTION

This invention relates to complexes of an amine salt of theophylline with zinc, their preparation and their use as a bronchodilator to treat bronchospasms.

More particularly, this invention relates to zinc complexes represented by the formula

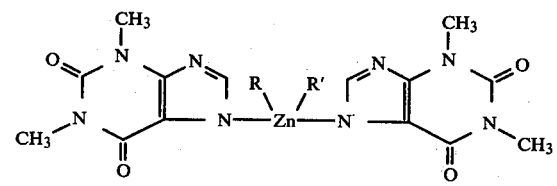

wherein R and R' are each a primary monoamine or ammonia or taken together are a lower alkyl primary diamine having from two to six carbon atoms.

The preferred primary amine is ethylenediamine.

The compounds of this invention have bronchodilator activity and can be administered in solid and liquid oral preparations, parenteral preparations, and suppositories. The zinc complexes are particularly suitable for oral preparations such as chewable tablets and suspensions because they are relatively insoluble and do not impart an unpleasant taste to the formulation. They are storage stable so that oral dosage forms containing the compounds as an active ingredient can be used after prolonged storage. In addition, the metal complexes of an amine salt of theophylline release theophylline in the stomach at a rate whereby acceptable therapeutic blood levels are reached and maintained over a relatively prolonged period.

If a solid enteric coated dosage form is used, then the theophylline is released in the small intestines, where the pH is sufficiently acidic to hydrolyze the complex. This will also enable the material to be released less rapidly than it would be under the more acidic conditions of the stomach.

The compounds of this invention are prepared by reacting simple water soluble salts of zinc, e.g. the chloride, sulfate or nitrate salts, with aqueous solutions of the amine salt of theophylline, e.g. aminophylline, or aqueous solutions of theophylline and a primary amine or ammonia.

DRAWINGS

DETAILED DESCRIPTION OF THE INVENTION

Figure 1:
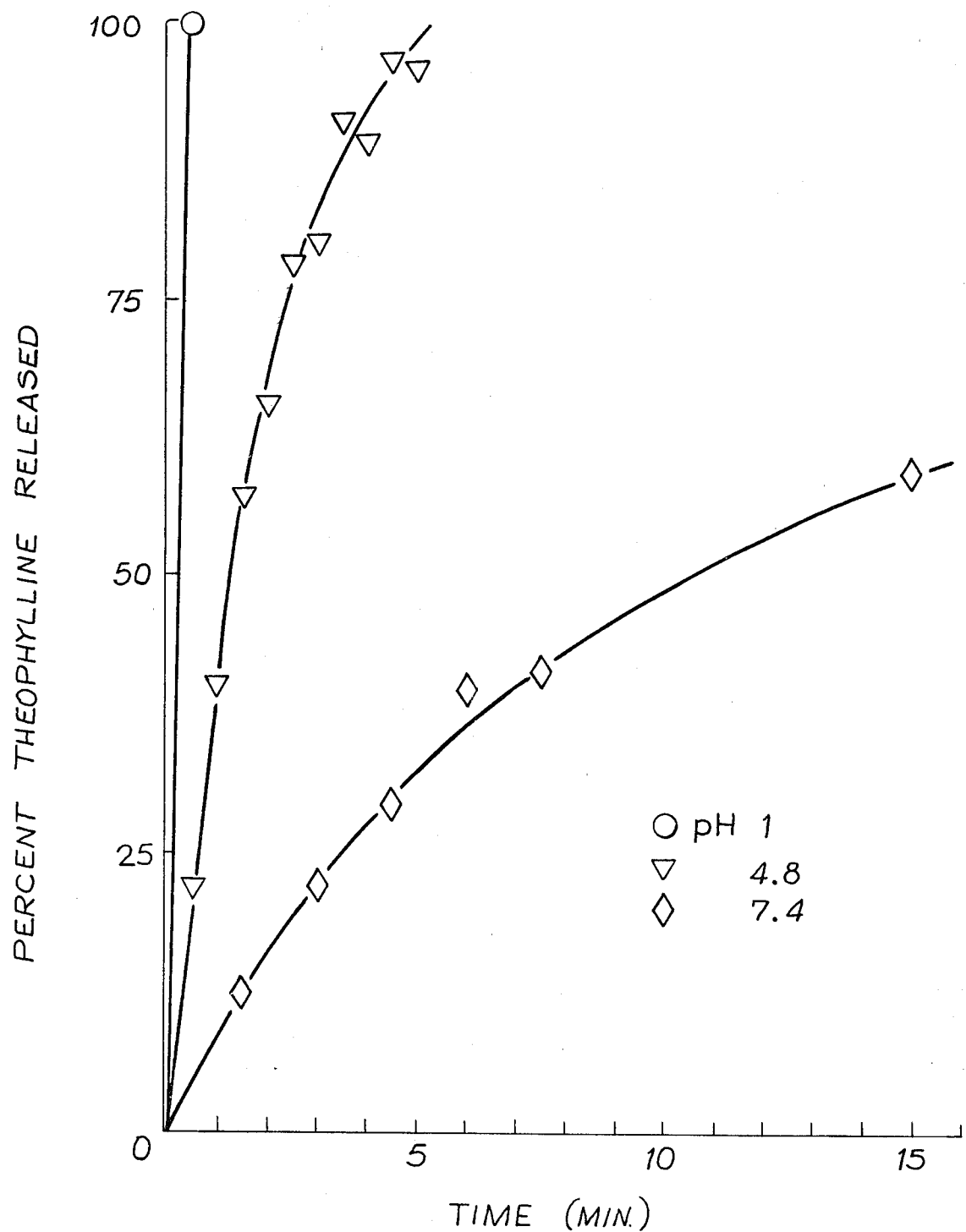
FIG. 1 is a graph showing the release rates of the zinc complex at different pH's into aqueous buffered solutions.

The complexes represented by Formula I are prepared by reacting a simple water soluble salt of zinc with either the amine salt of theophylline or theophylline and the amine in solution.

Zinc (II) is suitable for forming the complexes of this invention since it forms simple water soluble salts and complexes with a primary amine salt of theophylline in high yields to produce a tasteless, substantially insoluble compound with controllable solubility in the stomach and gastrointestinal tract.

The salts of zinc which are suitable are simple water soluble salts such as the chloride, sulfate, nitrate and the like. Generally the chloride or sulfate salts are preferred because they are readily available and are less costly.

Other metals which can form complexes with amine salts of the theophylline are di- and trivalent metals such as calcium, iron (II), iron (III), and magnesium. The number of the amine ligands attached to the metal are dependent on the coordination number of the particular metal.

The amines which are suitable are primary mono- and diamines which can form metal complexes and form amine salts with theophylline. Typical suitable amines are ammonia, monoethanolamine and ethylenediamine. Ethylenediamine is preferred because aminophylline is readily available.

The reaction conditions must be controlled to ensure best yields of the compounds of this invention. It is particularly important that the pH of the reaction mixture be kept between about 8 and 10, preferably pH 8.5 to 9. This ensures that the products are stable and will not hydrolyze, releasing theophylline.

When the starting material is an amine salt of theophylline, e.g. aminophylline, the aqueous solution to which it is added will become alkaline, with a pH between 8 and 10. The pH may be adjusted to be within this range with the amine. This is the preferred pH range for carrying out the reaction, as it is the range where these compleses will be most stable. The most preferred pH range is between 8.5 and 9.

An aqueous solution of the zinc salt is added to the theophylline-amine solution or amine salt of theophylline in solution. A reaction is allowed to take place during which a precipitate will form. The precipitate is colloidal in nature and heating is required to speed up crystal growth of the complex. The reaction is completed in about 8 to 16 hours at about 60° C. to 90° C. Generally the best yields are obtained in about 12 hours at about 80° C.

The amounts of the reagent used should be sufficient to complete the reaction. For example, the zinc complex of aminophylline contains 74% theophylline and 13.5% zinc, with the remainder ethylenediamine. In order to achieve a complete reaction, at least those relative amounts of reactants, e.g. one mole of zinc, one mole of ethylenediamine, and two moles of theophylline, should be present. Generally a larger amount of the amine is used to insure that no theophylline precipitates out of solution during the reaction.

The zinc complexes of this invention are less soluble in water than theophylline and its amine salts. The zinc complex of aminophylline is substantially insoluble at room temperature (25° C.) since an ultraviolet spectroscopy measurement of the amount of theophylline in a saturated solution at 25° C. revealed that only 85 micrograms per milliliter of theophylline is in solution. This complex is crystalline and exists as elongated monoclinic prisms.

Since the solubility of the zinc complex of aminophylline is very low, the material is tasteless either in solid or saturated solution form. It is, therefore, easily formulated into oral dosage forms such as suspensions or chewable tablets, the preferred dosage forms.

The complexes of this invention can be administered orally, parenterally, or as suppositories. The oral dosage forms can be tablets, dragees, capsules, or liquid suspensions. The tablets can be coated, uncoated, or chewable. The coating on the tablet can be a shellac or sugar coating or can be a sustained release or enteric coating.

In producing these pharmaceutical preparations, conventional pharmaceutically acceptable adjuvants and excipients, either organic or inorganic, are employed. Such adjuvants and excipients include water, gelatin, lactose, starches, magnesium stearate, talc, vegetable oils, gums, petroleum jelly, glycerol, ethyl alcohol, propylene glycol, polyalkylene glycols, and the like. Such pharmaceutical preparations may be in a unit dosage form and may additionally contain other conventional pharmaceutical adjuvants such as preservatives, buffers, and the like. The preparations may be submitted to conventional pharmaceutical expedients such as sterilization and the like. The only limitation on the formulation adjuvants and excipients are that they must be inert under the conditions of use, pharmaceutically acceptable, and compatible with the active agents.

The quantity of such excipients and adjuvants used in producing various dosage forms will vary depending upon the properties and characteristics of the excipients and adjuvants and the nature of the dosage forms to be formulated. In general, however, pharmaceutical preparations of the zinc complexes of this invention contain, in each unit dosage form, sufficient complex to provide the equivalent of about 50 mg of theophylline. In liquid suspensions, sufficient complex should be used to provide the equivalent of about 100 mg theophylline per 10 ml suspension. The amounts of the complex in these dosage forms represent quantities that can be used to effectively treat bronchospasms.

The complexes of this invention have the same spectrum of biological activity as theophylline, i.e., they can be used to relax smooth muscle, a property which enables them to be used for the symptomatic relief of bronchial asthma, pulmonary emphysema, chronic bronchitis, and other pulmonary diseases associated with bronchospasms.

The dosage amount and regimen used to give effective therapeutic response depends upon the condition of the patient and the judgment of the clinician. The usual pediatric dose for anhydrous theophylliny is 5 mg/kg of body weight every six hours. The total dose administered to children in a 24-hour period ordinarily should not exceed 20 mg theophylline per kg body weight. The adult dose usually is 200–300 mg of theophylline three or four times a day. Since, for example, the zinc complex of aminophylline is 74% by weight theophylline, appropriate adjustments should be made when determining the dosage regimen.

The following examples illustrate the invention.

EXAMPLE I 50 g theophylline are weighed into a 4-liter Ehrlenmeyer flask. To this is added 250 ml of an ethylenediamine solution (4.2% of ethylenediamine by volume in water). This resulting solution is diluted with water to 2½ liters. The pH of the solution should be 8.5 or higher, up to about 9. The resulting solution is warmed to approximately 60° C. to ensure complete dissolution of the theophylline. 250 ml of a 10% aqueous solution of zinc sulfate is added to the solution. When the zinc salt is added, the reaction mixture turns cloudy with the formation of a gel-type precipitate. The reaction flask is covered and heated to approximately 80° C. for 12 hours, or until crystals of the zinc complex are formed. The mixture is then cooled to room temperature. The crystals are collected by filtration and washed with cold water, then dried. The resulting product is composed of colorless elongated monoclinic prisms which are substantially insoluble in water. The zinc (II) ethylenediamine-theophylline complex salt, the preferred compound in this invention, which is formed contains 13.5% by weight zinc and has the empirical formula $ZnC_{16}N_{10}O_4H_{18}$. It decomposes at 405° C. without melting and a saturated aqueous solution has a pH 8.0–8.3.

Single crystal X-ray diffractometry was used to determine the molecular structure of the compound. It shows that there are two molecules of theophylline and one molecule of ethylenediamine coordinated to each zinc ion. The theophylline molecules are in the anionic form, i.e., they are negatively charged. The two amino functions of ethylenediamine are coordinated to the zinc. The ligands are tetrahedrally disposed about the zinc. The complex has a characteristic X-ray powder diffraction which is distinguishable from the materials from which it is formed. The ultraviolet absorption of acidic solutions of the compound are the same as that for theophylline. This indicates that the compound decomposes, releasing theophylline in acidic solutions.

When the product of Example I is placed in solutions with a pH lower than pH 8, it is hydrolyzed and neutral theophylline is released. In the pH range which is typical of the stomach, pH 1 to pH 4, the material rapidly releases theophylline. At pH's between 6 and 8 the dissolution and hydrolysis of the complex is slower. When 300 mg of the complex was added to 200 ml of buffered aqueous solutions at 25° C. with agitation, the theophylline release rates shown in FIG. 1 were obtained. It was observed that all of the theophylline in the complex added to the solution was released within a minute. At higher pH's the rate is slower. The release of theophylline from the complex when placed in the stomach will be much more rapid than its release in the intestines, where pH's are between 6 and 7. A much more protracted rate should be found in the intestines. The complex is stable in solutions between pH 8 and 9.

Figure 2:
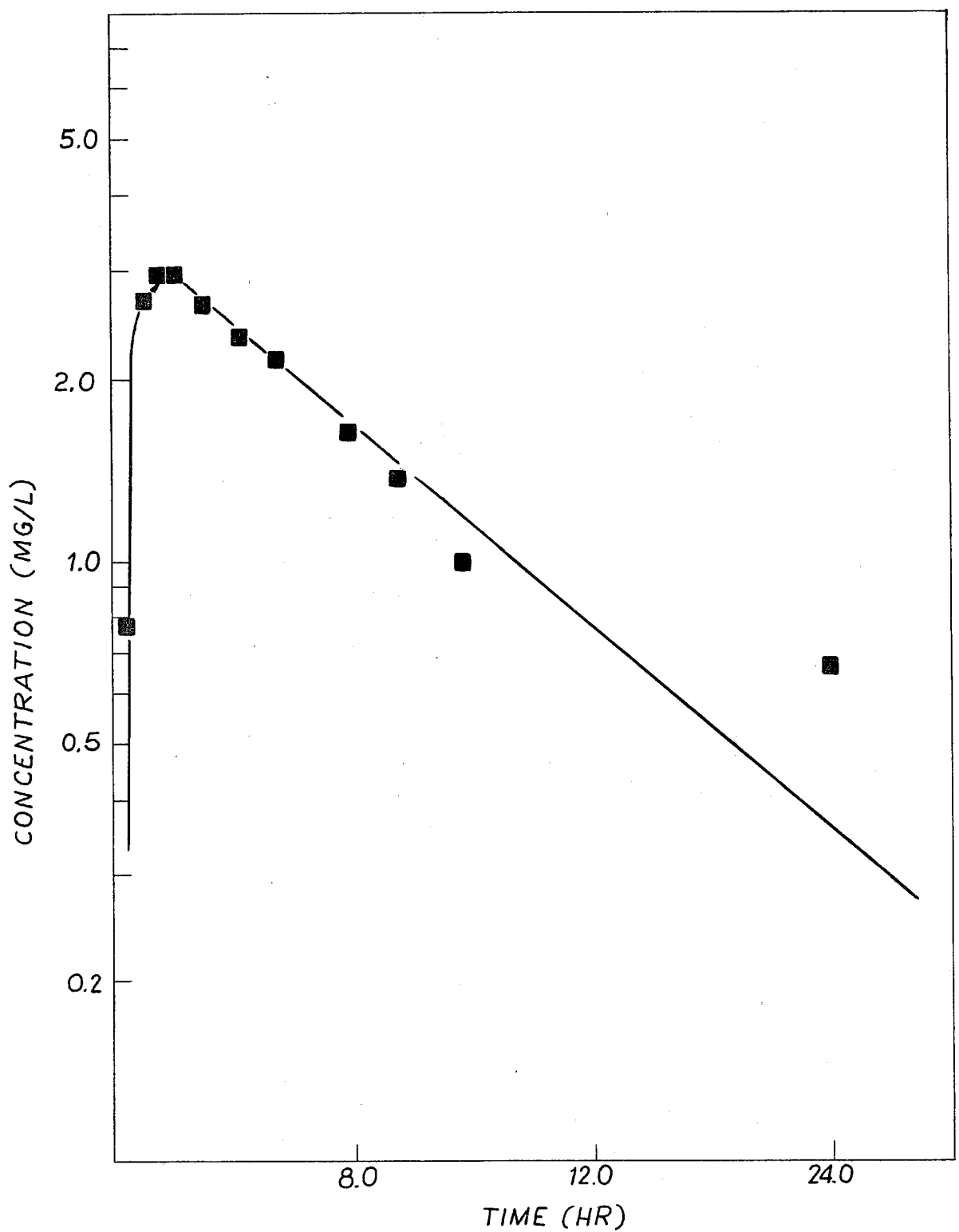
FIG. 2 is a graph showing saliva concentrations of theophylline after a single dose of the zinc complex is administered to a human subject.
Figure 3:
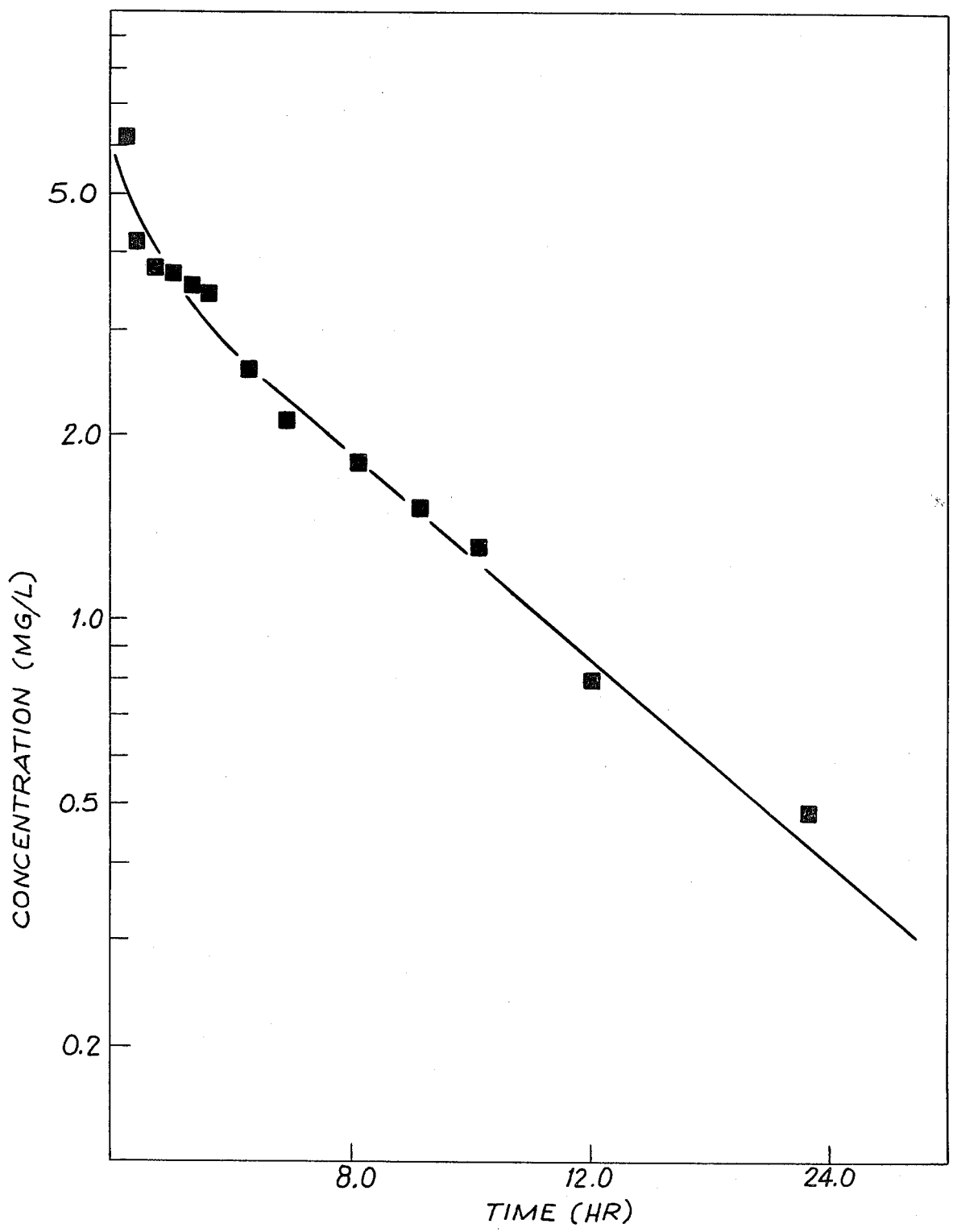
FIG. 3 is a graph showing saliva concentrations of theophylline after a single dose of anhydrous theophylline is administered to a human subject.

When the complex is administered orally, theophylline is released in the gastrointestinal tract and is subsequently absorbed. A male subject was administered a capsule containing 405 mg of the complex (equivalent to 300 mg theophylline) and at appropriate time intervals saliva samples were collected. The theophylline content of the saliva, which is proportional to serum concentration, was determined using a high performance liquid chromatographic procedure. The data obtained are shown in FIG. 2. A similar experiment was carried out with a capsule containing 300 mg of anhydrous theophylline. The data obtained are shown in FIG. 3. It was found that the theophylline released from the zinc complex is bioavailable and its absorption phase is slower than that exhibited for anhydrous theophylline. This slower absorption rate is due to a large extent to the low solubility of the complex which in turn influences the rate of dissolution and hydrolysis. The anhydrous theophylline produces a sharp peak concentration within one hour after administration. The peak concentration of the theophylline produced by the zinc complex is much broader and appears about two hours after administration.

Since theophylline has a narrow therapeutic range, serum concentrations above the therapeutic range can produce toxic side effects. It is important for patients taking maintenance doses not to go above the therapeutic range. As is demonstrated by FIG. 3, anhydrous theophylline's rapid absorption can produce a "spiking" effect, where for a short period the patient may have theophylline in the blood in the toxic range. With the slower absorption rate found for the compound produced in Example I, the "spiking" effect is minimized.

The administration of the compound produced in Example I did not produce any significant gastric distress to the subject. Since aminophylline is known to produce gastric distress when taken orally, the compound of this invention has an advantage over aminophylline in this regard.

The compound produced in Example I was stored under a variety of conditions and found to be stable. Humidity and temperatures up to 100° C. appear to have no adverse effect on the compound. Suspensions of the compound in water were stable. No change was detected in the structure of the suspended solids or the pH of the supernatant liquid when stored at room temperature. The suspension remained tasteless during long periods of storage.

EXAMPLE II

SUSPENSION FOR ORAL ADMINISTRATION

The following ingredients were used to form an aqueous suspension: 1.35 g of the zinc complex of aminophylline as the active ingredient, 1.5 g of Veegum HV* as the suspending agent, 30 ml of sucrose syrup U.S.P., 0.25 g of methyl paraben, 0.02 g of propyl paraben, 0.01 ml imitation chocolate oil, sufficient alkaline borate buffer solution (USP XIX) to adjust pH of system to 8.2 (range should be between 8.1 to 8.5) and sufficient water to make the suspension volume 100 ml.

*Veegum HV—colloidal magnesium aluminum silicate—R. T. Vanderbilt Company, New York, New York.

The above ingredients when combined together by pharmaceutically acceptable procedures will form an aqueous suspension containing 135 mg of active compound per 10 ml.

EXAMPLE III

CHEWABLE PEDIATRIC TABLET

The following ingredients were blended together in a sheer mixer and directly compressed into tablets to form chewable tablets containing 68 mg of the zinc complex of aminophylline per tablet as the active ingredient: 68 mg of zinc complex of aminophylline per tablet, 10 mg of pre-gelatinized starch, 1 mg of microsized synthetic silica, 0.2 mg of sodium saccharin, 0.4 mg of spray dried orange, and 28.4 mg of Nu-Tab (medium grade),* a direct compression sugar mixture containing small amounts of cornstarch and magnesium stearate.

*Nu-Tab—distributed by Mallinckrodt Chemical Works, St. Louis, Mo.

What is claimed is:

1. A compound represented by the formula

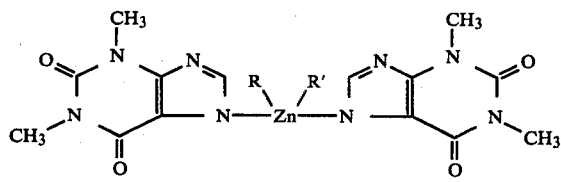

wherein R and R' are each a primary monoamine or ammonia or taken together are a lower alkyl primary diamine having from 2 to 6 carbon atoms.

2. The compound of claim 1, which is the zinc complex of aminophylline.

3. A chewable tablet containing an amount of the zinc complex of aminophylline which can be used to effectively treat bronchospasms and pharmaceutically acceptable tabletting adjuvants and excipients.

4. A pharmaceutical suspension suitable for oral administration containing an amount of the zinc complex of aminophylline which can be used to effectively treat bronchospasms and pharmaceutically acceptable oral suspension adjuvants and excipients.

5. A method of treating an asthmatic patient to relieve bronchospasms which comprises orally administering to said patient an effective amount of the composition of claim 3.

6. A method of treating asthmatic patients to relieve bronchospasms which comprises orally administering to said patient an effective amount of the composition of claim 4.

* * * * *